US011938184B2

(12) United States Patent
Agrawal

(10) Patent No.: US 11,938,184 B2
(45) Date of Patent: *Mar. 26, 2024

(54) COMPOSITIONS AND METHODS FOR TREATING CROHN'S DISEASE AND RELATED CONDITIONS AND INFECTIONS

(71) Applicant: Gaurav Agrawal, Manly (AU)

(72) Inventor: Gaurav Agrawal, Manly (AU)

(73) Assignee: Gaurav Agrawal, Manly (AU)

( * ) Notice: Subject to any disclaimer, the term of this patent is extended or adjusted under 35 U.S.C. 154(b) by 306 days.

This patent is subject to a terminal disclaimer.

(21) Appl. No.: 17/203,687

(22) Filed: Mar. 16, 2021

(65) Prior Publication Data

US 2021/0299254 A1 Sep. 30, 2021

Related U.S. Application Data

(63) Continuation of application No. 16/392,274, filed on Apr. 23, 2019, now Pat. No. 10,946,091, which is a (Continued)

(30) Foreign Application Priority Data

Jun. 4, 2012 (AU) .................................. 2012902307

(51) Int. Cl.
| | | |
|---|---|---|
| *A61K 39/395* | (2006.01) | |
| *A23C 9/123* | (2006.01) | |
| *A23G 3/36* | (2006.01) | |
| *A23G 4/06* | (2006.01) | |
| *A23G 4/12* | (2006.01) | |
| *A23G 9/32* | (2006.01) | |
| *A23G 9/36* | (2006.01) | |
| *A61K 31/133* | (2006.01) | |
| *A61K 31/4164* | (2006.01) | |
| *A61K 31/435* | (2006.01) | |
| *A61K 31/496* | (2006.01) | |
| *A61K 31/498* | (2006.01) | |
| *A61K 31/7048* | (2006.01) | |
| *A61K 33/00* | (2006.01) | |

(Continued)

(52) U.S. Cl.
CPC ........ *A61K 39/39533* (2013.01); *A23C 9/123* (2013.01); *A23G 3/36* (2013.01); *A23G 3/364* (2013.01); *A23G 4/06* (2013.01); *A23G 4/12* (2013.01); *A23G 9/32* (2013.01); *A23G 9/36* (2013.01); *A61K 31/133* (2013.01); *A61K 31/4164* (2013.01); *A61K 31/435* (2013.01); *A61K 31/496* (2013.01); *A61K 31/498* (2013.01); *A61K 31/7048* (2013.01); *A61K 33/00* (2013.01); *A61K 39/3955* (2013.01); *A61K 39/40* (2013.01); *A61K 2039/505* (2013.01); *Y02A 50/30* (2018.01)

(58) Field of Classification Search
CPC ............ A61K 39/3955; A61K 2300/00; A61K 39/39533; A61K 31/133; A61K 31/4164; A61K 31/435; A61K 31/496; A61K 31/498; A61K 31/7048; A61K 33/00; A61K 39/40; A61K 2039/505; A61P 1/00
See application file for complete search history.

(56) References Cited

U.S. PATENT DOCUMENTS 9,616,121 B2 * 4/2017 Agrawal ................. A61P 29/00
10,376,578 B2 * 8/2019 Agrawal ................. A61K 33/00
(Continued)

FOREIGN PATENT DOCUMENTS

WO 2007120720 A2 10/2007

OTHER PUBLICATIONS

Dong, Ji Liu, The State Intellectual Property Office of the People's Republic of China Office Action dated Oct. 23, 2015, 7 pages.
Hermon-Taylor, John, "*Mycobacterium avium* subspecies paratuberculosis, Crohn's disease and the Doomsday Scenario", Gut Pathogens 1:15, (2009), 6 pages.
Katsanos, Konstantinos H., et al., "Fournier's gangrene complicating ulcerative pancolitis", Journal of Crohn's and Colitis, 4, (2010), pp. 203-206.

(Continued)

*Primary Examiner* — Aradhana Sasan
(74) *Attorney, Agent, or Firm* — Greer, Burns & Crain, Ltd.; Gregory P. Einhorn

(57) ABSTRACT

In alternative embodiments, the invention provides a "triple combination" therapy for treating, ameliorating and preventing Crohn's Disease (or Crohn syndrome, terminal or distal ileitis or regional enteritis) or related disorders and conditions in mammals, such as paratuberculosis in mammals, or Johne's disease, including genetically-predisposed and chronic disorders, where the microbial or bacterial flora of the bowel is at least one causative or symptom-producing factor; and compositions for practicing same. In alternative embodiments, methods and compositions of the invention comprise or comprise use of therapies, medications, formulations and pharmaceuticals comprising active agents that can suppress or eradicate the microbiota super-infection that causes Crohn's Disease or paratuberculosis infection in mammals. In alternative embodiments, the methods and uses of the invention for treating, ameliorating and preventing Crohn's Disease and complications of Crohn's Disease, or related disorders and conditions in mammals, such as paratuberculosis in mammals, or Johne's disease, comprises administration to an individual (human or mammal) in need thereof: (1) an anti-TNFα composition, or a composition capable of down-modulating TNFα activity; (2) a Hyperbaric Oxygen Treatment, or HBOT; and (3) an anti *Mycobacterium avium* sub species *paratuberculosis* (MAP) (an anti-MAP) agent, composition or therapy.

24 Claims, 4 Drawing Sheets

Related U.S. Application Data continuation-in-part of application No. 15/483,702, filed on Apr. 10, 2017, now Pat. No. 10,376,578, which is a continuation of application No. 14/405,384, filed as application No. PCT/AU2013/000587 on Jun. 3, 2013, now Pat. No. 9,616,121.

(51) Int. Cl.
*A61K 39/00* (2006.01)
*A61K 39/40* (2006.01)

(56) References Cited

U.S. PATENT DOCUMENTS

| | | | | |
|---|---|---|---|---|
| 10,946,091 | B2* | 3/2021 | Agrawal | A23G 4/12 |
| 2010/0004157 | A1* | 1/2010 | Ajani | A61K 9/2054 |
| | | | | 514/1.1 |

OTHER PUBLICATIONS

Loher, Florian, European Patent Office Examiner's Report dated Mar. 16, 2016, 7 pages.
West, R.L., et al., "Clinical and endosonographic effect of ciprofloxacin on the treatment of perianal fistulae in Crohn's disease with infliximab: a double-blind placebo-controlled study", Aliment Pharmacol Ther, 20 (2004), pp. 1329-1336.
Dong, Liu, The State Intellectual Property Office of the People's Republic of China Second Office Action, Application No. 2013800409233, dated Jul. 1, 2016, 13 pages.
Lavy, A., et al., "Hyperbaric Oxygen for Perianal Crohn's Disease", J Clin Gastroenterol, 19(3), (1994), pp. 202-205.
Rossignol, Daniel A., "Hyperbaric oxygen treatment for inflammatory bowel disease: a systematic review and analysis", J Medical Gas Research, 2:6, Mar. 15, 2012, 28 pages.
Dalton, International Search Report and Written Opinion, PCT/AU2013/00587, dated Sep. 10, 2013.
Jiang et al., "Fournier gangrene associated with Crohn's disease", Mayo Clin. Proc., 2000, v 75, n 6, p. 647-649.
Nicktias-Etienne, International Preliminary Report on Patentability, PCT/AU2013/00587 dated Dec. 18, 2014.
Nelson et al., "Closure of refractory perineal Crohn's lesion. Integration of hyperbaric oxygen into case management", Dig Dis Sci, 1990, v 35, n 12, p. 1561-1565.
Yamamoto, Notice of Reasons for Rejection for Japanese Patent Application 2015-515351, dated Mar. 16, 2017.
Nakase et al., "Involvement of *Mycobacterium avium* subspecies Paratuberculosis in TNF-alpha Production from Macrophage" Inflammatory Bowel Disease, Nov. 2011, v 17, n 11.
Bach, "Treatment of Crohn's disease patients with infliximab is detrimental for the survival of *Mycobacterium avium* ssp. paratuberculosis within macrophages and shows a remarkable decrease in the immunogenicity of mycobacterial proteins", Journal of Crohn's and Colitis 2012, v 6, p. 628-629.
Behr et al., "The evidence for *Mycobacterium paratuberculosis* in Crohn's disease" Current Opinion in Gastroenterology, 2007.
Marimon et al., "An oxygen-sensitive toxin-antitoxin system", Apr. 1, 2016, DOI: 10.1038/ncomms13634.
Mcnees et al., "*Mycobacterium paratuberculosis* as a cause of Crohn's disease" Oct. 15, 2015, Expert Rev. Gastroenterol. Hepatol., v 9, n 12, p. 1523-1534.
O'Brien, Response filed on Oct. 10, 2017 to Examiner's Report issued for AU 2013271336 dated Jun. 23, 2017.
Dalton, Examination Report No. 1 for AU 2013271336 dated Jun. 23, 2017.
O'Brien, Response filed on Dec. 14, 2016 to Examiner's Report issued for NZ 703394 dated Sep. 7, 2016.
Jebson, Examiner's Report issued for NZ 703394 dated Sep. 7, 2016.
O'Brien, Response filed on Aug. 10, 2016 to Examiner's Report issued for NZ 703394 dated Jan. 12, 2016.
Jebson, Examiner's Report issued for NZ 703394 dated Jan. 12, 2016.
Sannabe Notice of Reasons for Rejection for JP 2015-515351 dated Apr. 6, 2018.
Reexamination Notification for Chinese Application CN 201380040923.3 dated Sep. 21, 2018.
Robert T. Lewis et al., Efficacy and Complications of Surgery for Crohn's Disease, Gastroenterology & Hepatology (NY).Sep. 2010; 6 (9): 587-596.
Takayuki Yamamoto, Prevention of recurrence after surgery for Crohn's disease: Efficacy of infliximab, World Journal of Gastroenterology Nov. 21, 2010; 16 (43); 5405-5410.
Simon Lal et al., Antibiotic therapy for Crohn's disease: A review, Can J Gastroenterol, 2006; 20(10): 651-655.
Agrawal et al., Combining infliximab, anti-MAP and hyperbaric oxygen therapy for resistant fistulising Crohn's disease, Future Science, 2015.
Sannabe, English Translation of Penultimate Official Action for JP Patent Application 2018-191046 dated Apr. 23, 2020.
Borody et al., "Resistant fistulizing corhns disease treated with combination of infliximab, anti-MAP and hyperbaric oxygen (HBO)" The American Journal of Gastroenterology, 2012, v 107, supplement 1, S670.
Gnarpe et al., "Influence of metronidazole and tinidazole on leukocyte chemotaxis in Crohn's disease" Infection, 1978, 6, supplement 1, p. 107-110.

* cited by examiner

Pre triple therapy. Multiple fistulae

Completely healed mucosa Post tx

Pre tx. Recto vaginal fistula

Completely healed mucosa Post tx

COMPOSITIONS AND METHODS FOR TREATING CROHN'S DISEASE AND RELATED CONDITIONS AND INFECTIONS

CROSS-REFERENCE TO RELATED APPLICATIONS

This United States Utility Patent Application is a continuation of U.S. Utility patent application Ser. No. 16/392,274, filed Apr. 22, 2019, now U.S. Pat. No. 10,946,091, which is a continuation-in-part (CIP) of U.S. Utility patent application Ser. No. 15/483,702, filed Apr. 10, 2017, now U.S. Pat. No. 10,376,578 which is a continuation of U.S. Ser. No. 14/405,384, filed Dec. 3, 2014, now U.S. Pat. No. 9,616,121, issued Apr. 11, 2017, which claims benefit of priority to and is a § 371 national phase of Patent Cooperation Treaty Application Number CT/AU2013/000587, having an international filing date of Jun. 4, 2013, which claims benefit of priority to Australian Patent Application Serial Number 2012902307, filed Jun. 4, 2012. The aforementioned applications are expressly incorporated by reference in their entirety and for all purposes.

TECHNICAL FIELD

This invention generally relates to medicine and gastroenterology, pharmacology and microbiology. In alternative embodiments, the invention provides a "triple combination" therapy for treating, ameliorating and preventing Crohn's Disease (or Crohn syndrome, terminal or distal ileitis or regional enteritis) or related disorders and conditions in mammals, such as paratuberculosis in mammals, or Johne's disease, including genetically-predisposed and chronic disorders, where the microbial or bacterial flora of the bowel is at least one causative or symptom-producing factor; and compositions for practicing same. In alternative embodiments, methods and compositions of the invention comprise or comprise use of therapies, medications, formulations and pharmaceuticals comprising active agents that can suppress or eradicate the microbiota super-infection that causes Crohn's Disease or paratuberculosis infection in mammals. In alternative embodiments, the methods and uses of the invention for treating, ameliorating and preventing Crohn's Disease and complications of Crohn's Disease, or related disorders and conditions in mammals, such as paratuberculosis in mammals, or Johne's disease, comprises administration to an individual (human or mammal) in need thereof: (1) an anti-TNFα composition, or a composition capable of down-modulating TNFα activity; (2) a Hyperbaric Oxygen Treatment, or HBOT; and (3) an anti *Mycobacterium avium* sub species *paratuberculosis* (MAP) (an anti-MAP) agent, composition or therapy.

BACKGROUND

Crohn's disease is a chronic inflammatory condition most likely caused by some form of infection. The most likely infective agent is *Mycobacterium avium* sub species *paratuberculosis* (MAP). Other infective agents that may cause Crohn's disease are *Mycobacterium tuberculosis*—indistinguishable from Crohn's disease; *Entamoeba histolytica, Escherichia coli, Yersinia enterocolitica* & atypical *Campylobacter* species. Current therapies aim at reduction of inflammation but there is an emerging trend to treat the underlying infection.

Infliximab can suppress a particular segment of the immune system and exert similar effects in suppressing inflammation as azathioprine, 6-mercapto-purine, Methotrexate and Prednisone. Infliximab can have antimicrobial activity against MAP and MAP containing bacteria. Anti-*Mycobacterium paratuberculosis* (Anti-MAP) therapy can heal Crohn's disease successfully, however healing time can be delayed and may take quite a few weeks or months even to induce remission. Anti-MAP Therapy can be slower in acting. When combined with immunosuppressants, such as azathioprine or 6-mercapto-purine, antibiotics do not work as they could in Crohn's disease—possibly due to the inhibition of the endogenous immunity.

SUMMARY

In alternative embodiments, the invention provides methods, treatments or "triple combination" therapies, for treating, ameliorating and/or preventing a Crohn's Disease, or a complication of a Crohn's Disease, or a Crohn's Disease-related fistulae, or related disorders and conditions in mammals, such as paratuberculosis in mammals, or Johne's disease, comprising administration to an individual, a mammal, or a patient in need thereof:
  (1) an anti-TNFα composition or drug, or a composition or a drug capable of down-modulating or down-regulating a TNFα activity;
  (2) a Hyperbaric Oxygen Treatment, or HBOT, or the medical use of oxygen at a level higher than atmospheric pressure; and
  (3) an anti *Mycobacterium avium* sub species *paratuberculosis* (MAP) (also called *M. paratuberculosis* or *M. avium* ssp.) (an anti-MAP) agent, composition, drug or therapy.

In alternative embodiments of the methods, treatments or "triple combination" therapies of the invention:
  (a) the TNFα activity comprises causing an autophagy or an apoptosis in a cell;
  (b) the anti-TNFα composition or drug, or the composition or drug capable of down-modulating or down-regulating a TNFα activity, comprises a protein, a peptide or an antibody capable of specifically binding to a TNFα or a TNFα-receptor or TNFα downstream effector;
  (c) the method, treatment or "triple combination" therapy of (b), wherein antibody is or comprises: an infliximab or a REMICADE™ (Janssen Biotech, Inc.); an adalimumab or a HIJIViIRA™ (Abbvie, North Chicago, Ill.); a certolizumab, certolizumab pegol or a CIMZIA™; a golimumab or a SIMPONI™; a basiliximab or a SIMULECT™; a daclizumab or a ZENAPAX™; an omalizumab or a XOLAIR™; or, any combination thereof;
  (d) the Hyperbaric Oxygen Treatment or the medical use of oxygen at a level higher than atmospheric pressure, comprises use or administration of:
  a pressure of about 100% oxygen,
  between about 90% and 100% oxygen,
  oxygen at about 2.5 atm absolute, or between about 2 and 3 atm absolute, or
  oxygen for about 90 minutes or for between about 1 hour and 2 hours per session or treatment, or
  any combination thereof;
  (e) the anti *Mycobacterium avium* sub species *paratuberculosis* (MAP) agent, composition, drug or therapy, comprises administration of:
  (1) a macrolide antibiotic;
  (2) a rifabutin and a macrolide antibiotic;

(3) a rifabutin or a MYCOBUTIN™, a macrolide antibiotic, and a clofazimine;
(4) a combination of a rifabutin, a clarithromycin and a clofazimine or a LAMPRENE™;
(5) any of (1) to (4), wherein the macrolide antibiotic is or comprises:
   a clarithromycin, or a TRUCLAR™, CRIXAN™, CLARITT™, CLARAC™, BIAXIN™, KLARICID™, KLACID™, KLARAM™, KLABAX™, CLARIPEN™, CLAREM™, CLARIDAR™, FROMILID™, CLACID™, CLACEE™, VIKROL™, INFEX™, CLARIWIN™, RESCLAR™, RANBAXY™ or a CLARIHEXAL™;
   a dirithromycin, or a DYNABAC™;
   a roxithromycin or a XTHROCIN™, ROXL-150™, ROXO™, or a SURLID™;
   a telithromycin or a KETEK™;
   an azithromycin, a ZITHROMAX™ or a AZITHROCIN™;
   a troleandomycin, a TRIOCETIN™, or a TEKMISIN™; or
   a mixture or combination thereof;
(6) a nitroimidazole antibiotic, a metronidazole, a 5-nitroimidazole, or a FLAGYL™;
(7) a fluoroquinolone antibiotic, a ciprofloxacin, a CILOXAN™, a CIPRO™, or a NEOFLOXIN™;
(8) a nitroimidazole antibiotic, a metronidazole or a 5-nitroimidazole;
(9) a fluoroquinolone antibiotic or a ciprofloxacin;
(10) a nitroimidazole antibiotic, a metronidazole or a 5-nitroimidazole and a fluoroquinolone antibiotic or a ciprofloxacin;
(11) a rifaximin, a XIFAXAN™, a XIFAXANTA™, a NORMIX™, a rifamycin or a rifamycin B;
(12) a rifampicin, a RIFADIN™, a rifadine, a rimycin, a EREMFAT™, a RIMACTANE™, a RIFINAH™, a pyrazinamide or RIFATER™, optionally with an isoniazid, LANIAZID™ or NYDRAZID™; or a rifampicin, a RIFADIN™, a rifadine, a rimycin, a EREMFAT™, a RIMACTANE™, or a RIFINAH™ with a pyrazinamide or RIFATER™ and/or an isoniazid, LANIAZID™ or NYDRAZID™;
(13) an anti-TNFα composition or drug, or a composition or a drug capable of down-modulating or down-regulating a TNFα activity (in one embodiment an anti-TNFα composition or drug is used as the sole anti-MAP agent, and in this embodiment the method, treatment or therapy comprises use of two agents, albeit with three functions);
(14) a mixture or a combination of any one or several of (1) to (13);
(f) the anti-TNFα composition or drug, or a composition or a drug capable of down-modulating or down-regulating a TNFα activity of (1); the Hyperbaric Oxygen Treatment, or HBOT, or the medical use of oxygen at a level higher than atmospheric pressure of (2); and the anti-MAP agent, composition, drug or therapy of (3) are administered simultaneously;
(g) the anti-TNFα composition or drug, or a composition or a drug capable of down-modulating or down-regulating a TNFα activity of (1) is administered before, during, or after, or in between sessions of, the Hyperbaric Oxygen Treatment, or HBOT, or the medical use of oxygen at a level higher than atmospheric pressure of (2), and the anti-MAP agent, composition, drug or therapy of (3);
(h) the anti-MAP agent, composition, drug or therapy of (3) is administered before, during, or after, or in between sessions of, the Hyperbaric Oxygen Treatment, or HBOT, or the medical use of oxygen at a level higher than atmospheric pressure of (2), and the anti-TNFα composition or drug, or a composition or a drug capable of down-modulating or down-regulating a TNFα activity of (1); or
(i) the Hyperbaric Oxygen Treatment, or HBOT, or the medical use of oxygen at a level higher than atmospheric pressure of (2) is administered before, during, or after, or in between sessions of, the anti-TNFα composition or drug, or a composition or a drug capable of down-modulating or down-regulating a TNFα activity of (1) and the anti-MAP agent, composition, drug or therapy of (3).

In alternative embodiments of the methods, treatments or "triple combination" therapies of the invention:
   an anti-MAP or an anti-TNFα composition, drug, formulation, pharmaceutical or pharmaceutical preparation is formulated as a chewable delivery vehicle, a gum, a gummy, a candy, a lozenge, an ice cream or an ice, or a yogurt, a unit dosage of an anti-MAP or an anti-TNFα composition, drug, formulation, pharmaceutical or pharmaceutical preparation is formulated as a pediatric unit dosage;
   a unit dosage of an anti-MAP or an anti-TNFα composition, drug, formulation, pharmaceutical or pharmaceutical preparation is formulated as unit dosage between about 10 mg and 1100 mgm, or is about 10, 20, 30, 40, 50, 60, 70, 75, 80, 90, 100, 125, 150, 175, 200, 225, 250, 275, 300, 325, 350, 375, 400, 425, 450, 475, 500, 600, 700, 750, 800, 900, 1000 or 1100 or more mg per unit dose,
   a unit dosage of an anti-MAP or an anti-TNFα composition, drug, formulation, pharmaceutical or pharmaceutical preparation is formulated or administered for a daily or once a day dosage of about 100, 125, 150, 175, 200, 225, 250, 275, 300, 325, 350, 375, 400, 425, 450, 475, 500, 600, 700, 750, 800, 900, 1000 or 1100 or more mg per day, or between about 100 and 1100 mgm per day,
   a unit dosage of an anti-MAP or an anti-TNFα composition, drug, formulation, pharmaceutical or pharmaceutical preparation is administered or set for a bid (twice a day), tid (three times a day), four times a day, five times a day or six times a day or more, and optionally with the unit dosage and daily dosage adjusted to be: about 1000 mg/70 kg a day, or about 14 mg/kg a day, for an adult median dose per day (or, e.g., five times a day for adult use, or for a 70 kg individual would be 200 mg per unit dose); or for a pediatric dosage about 350 mg/25 kg a day, or about 15 to 16 mg/kg, a day; or equivalent (or, e.g., so five times a day for pediatric use, or for a 25 kg individual, would be 70 mg per unit dose).

In alternative embodiments of the methods, treatments or "triple combination" therapies of the invention, the anti-MAP or an anti-TNFα composition, drug, formulation, pharmaceutical or pharmaceutical preparation further comprises or has added to:
   a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof;
   a preservative, a benzoic acid, a potassium sorbate;

at least one probiotic or prebiotic, wherein optionally the prebiotic comprises an inulin, lactulose, extracts of artichoke, chicory root, oats, barley, various legumes, garlic, kale, beans or flax or an herb, wherein optionally the probiotic comprises a cultured or stool-extracted microorganism or bacteria, or a bacterial component, and optionally the bacteria or bacterial component comprises or is derived from a *Bacteroidetes*, a *Firmicutes*, a *Lactobacilli*, a *Bifidobacteria*, an *E coli*, a *Strep fecalis* and equivalents;

at least one congealing agent, wherein optionally the congealing agent comprises an arrowroot or a plant starch, a powdered flour, a powdered potato or potato starch, an absorbant polymer, an Absorbable Modified Polymer (AMP™), ENDOCLOT™ (Santa Clara, Calif.), and/or a corn flour or a corn starch;

at least one an anti-inflammatory agent, wherein optionally the inflammatory agent comprises or is a 4 or a 5-amino-salicylate, an olsalazine (e.g., DIPENTUM™), a mesalazine (also known as mesalamine or a 5-aminosalicylic acid (5-ASA), e.g., ASACOL™ or LIALDA™), a sulfasalazine (e.g., AZULFIDINE™ SALAZOPYRIN™ or SULAZINE™), and/or a balsalazide (e.g. COLAZAL™ or COLAZIDE™), or an equivalent thereof or a combination thereof;

an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient; or at least one Biofilm Disrupting Compound, wherein optionally the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea furanones*, N-sulfonyl homoserine lactones or any combination thereof.

In alternative embodiments, the anti-MAP or an anti-TNFα composition, drug, formulation, pharmaceutical or pharmaceutical preparation: is formulated as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly(meth)acrylate, e.g. a methacrylic acid copolymer B, NF, such as EUDRAGIT S™ (Evonik Industries AG, Essen, Germany), which dissolves at pH 7 or greater, e.g., comprises a multimatrix (MMX) formulation.

In alternative embodiments, the anti-MAP or an anti-TNFα composition, drug, formulation, pharmaceutical or pharmaceutical preparation further comprises or has added to:

an additional antimicrobial or an antibiotic, wherein optionally the additional antimicrobial or an antibiotic comprises:

an ampicillin, a sulbactama tetracycline, a cephalosporin, a carbapenem, an imipenem, a meropenem, a MONAN™, MERONEM™, a monobactam, a lincosamide, a clindamycin, a DALACIN™, a quinolone, a fluoroquinolone, a sulphonamide, a fradicin, a NEO-BIOTIC™, a nitroimidazole, a metronidazole, a tinidazole, an anti-clostridial agent, or a ramoplanan, an aminoglycoside antibiotic, a gentamycin, a neomycin, a streptomycin, a paromomycin, a verdamicin, a mutamicin, a sisomicin, a netilmicin, a retymicin, a kanamycin, an amphenicol, an ansamycin, a beta-lactam (β-lactam) antibiotic, a carbapenem, a cephalosporin, a cephamycin, a monobactam, an oxacephem, a lincosamide antibiotic, a clindamycin, or a lincomycin, a glycopeptide antibiotic, a vancomycin, a teicoplanin, a telavancin, a bleomycin, a ramoplanin, a decaplanin, a polypeptide antibiotic, an actinomycin, an actinomycin D, a bacitracin, a bacitracin, a tetracycline, a 2,4-diaminopyrimidine class antibiotic, a clavacin, a clairformin, a claviform, an expansine, a clavatin, an expansin, a gigantin, a leucopin, a patuline or a patulin, or an equivalent thereof or a combination thereof.

In alternative embodiments, the invention provides a delivery vehicle, product of manufacture, container, syringe, device or bag, comprising: an anti-MAP and an anti-TNFα composition, drug, formulation, pharmaceutical or pharmaceutical preparation dosaged for administration to an individual, a mammal or a patient for practicing a method of the invention.

In alternative embodiments, the invention provides a delivery vehicle, pharmaceutical preparation, product of manufacture, container, bag or device comprising: an anti-MAP and an anti-TNFα composition, drug, formulation, pharmaceutical or pharmaceutical preparation dosaged for administration to an individual, a mammal or a patient for practicing a method of the invention, optionally manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

In alternative embodiments, the invention provides uses of:

(1) an anti-TNFα composition or drug, or a composition or a drug capable of down-modulating or down-regulating a TNFα activity; and (2) an anti *Mycobacterium avium* sub species *paratuberculosis* (MAP) (an anti-MAP) agent, composition, drug or therapy, in the preparation of a medicament for treating, ameliorating and/or preventing a Crohn's Disease, or a complication of a Crohn's Disease, or a Crohn's Disease-related fistulae, or related disorders and conditions in mammals, such as paratuberculosis in mammals, or Johne's disease.

In alternative embodiments, the invention provides a therapeutic combination of drugs comprising or consisting of a combination of at least two compounds: wherein the at least two compounds comprise or consist of:

(1) an anti-TNFα composition or drug, or a composition or a drug capable of down-modulating or down-regulating a TNFα activity; and (2) an anti *Mycobacterium avium* sub species *paratuberculosis* (MAP) (an anti-MAP) agent, composition, drug or therapy, wherein the therapeutic combination is formulated or dosage for treating, ameliorating and/or preventing a Crohn's Disease, or a complication of a Crohn's Disease, or a Crohn's Disease-related fistulae, or related disorders and conditions in mammals, such as paratuberculosis in mammals, or Johne's disease.

In alternative embodiments, the invention provides a combination for treating, ameliorating and/or preventing a Crohn's Disease, or a complication of a Crohn's Disease, or a Crohn's Disease-related fistulae, or related disorders and conditions in mammals, such as paratuberculosis in mammals, or Johne's disease, comprising:

(1) an anti-TNFα composition or drug, or a composition or a drug capable of down-modulating or down-regulating a TNFα activity; and (2) an anti-*Mycobacterium avium* sub species *paratuberculosis* (MAP) (an anti-MAP) agent, composition, drug or therapy, wherein the therapeutic combination is formulated or dosage.

In alternative embodiments, the invention provides a therapeutic combination for treating, ameliorating and/or preventing a Crohn's Disease, or a complication of a Crohn's Disease, or a Crohn's Disease-related fistulae, or related disorders and conditions in mammals, such as paratuberculosis in mammals, or Johne's disease, comprising:

(1) an anti-TNFα composition or drug, or a composition or a drug capable of down-modulating or down-regulating a TNFα activity;

(2) a Hyperbaric Oxygen Treatment, or HBOT, or the medical use of oxygen at a level higher than atmospheric pressure; and (3) an anti *Mycobacterium avium* sub species *paratuberculosis* (MAP) (also called *M. paratuberculosis* or *M. avium* ssp.) (an anti-MAP) agent, composition, drug or therapy.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

Figure 1:
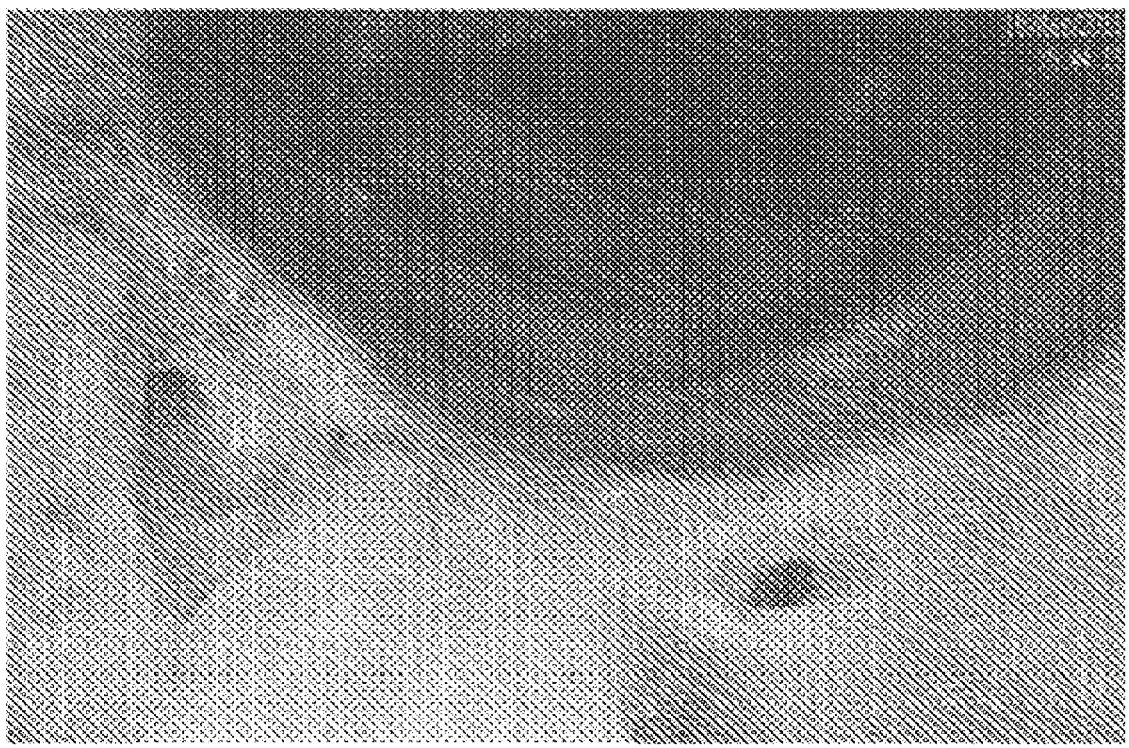
FIG. 1 illustrates an image of a multiple fistulae before treatment with an exemplary Pre triple therapy as provided herein.
Figure 2:
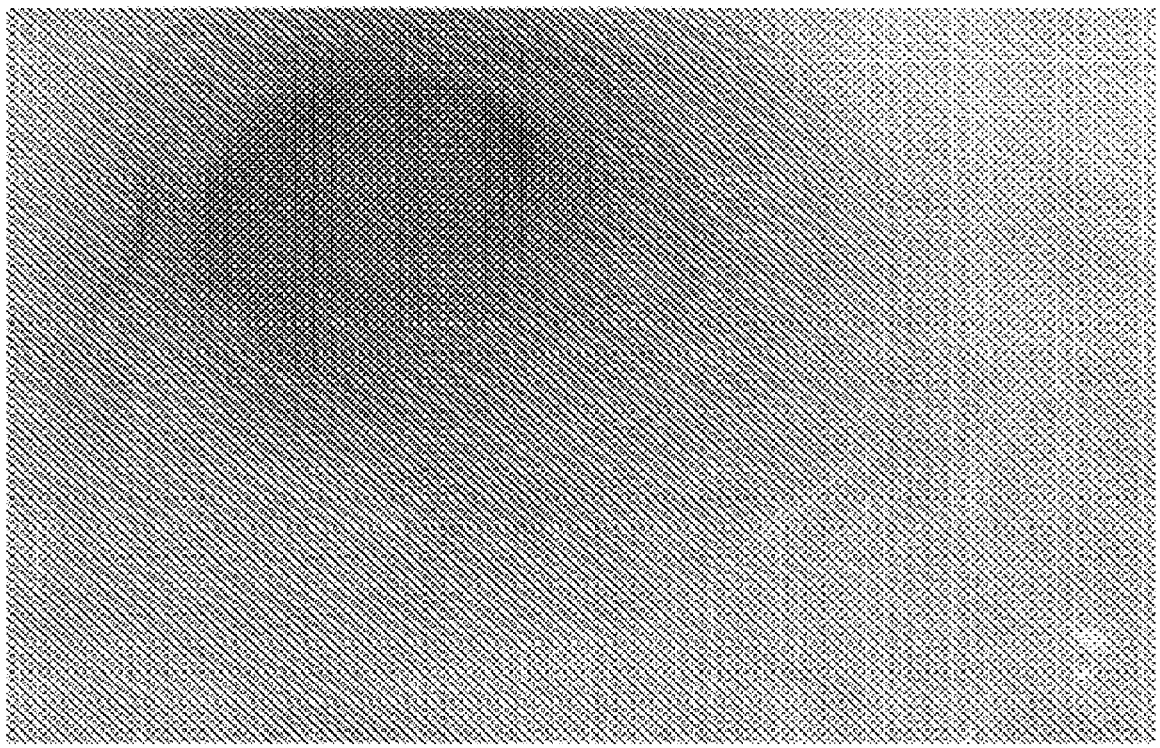
FIG. 2 illustrates an image of a completely healed mucosa after treatment of the multiple fistulae with an exemplary Pre triple therapy as provided herein.
Figure 3:
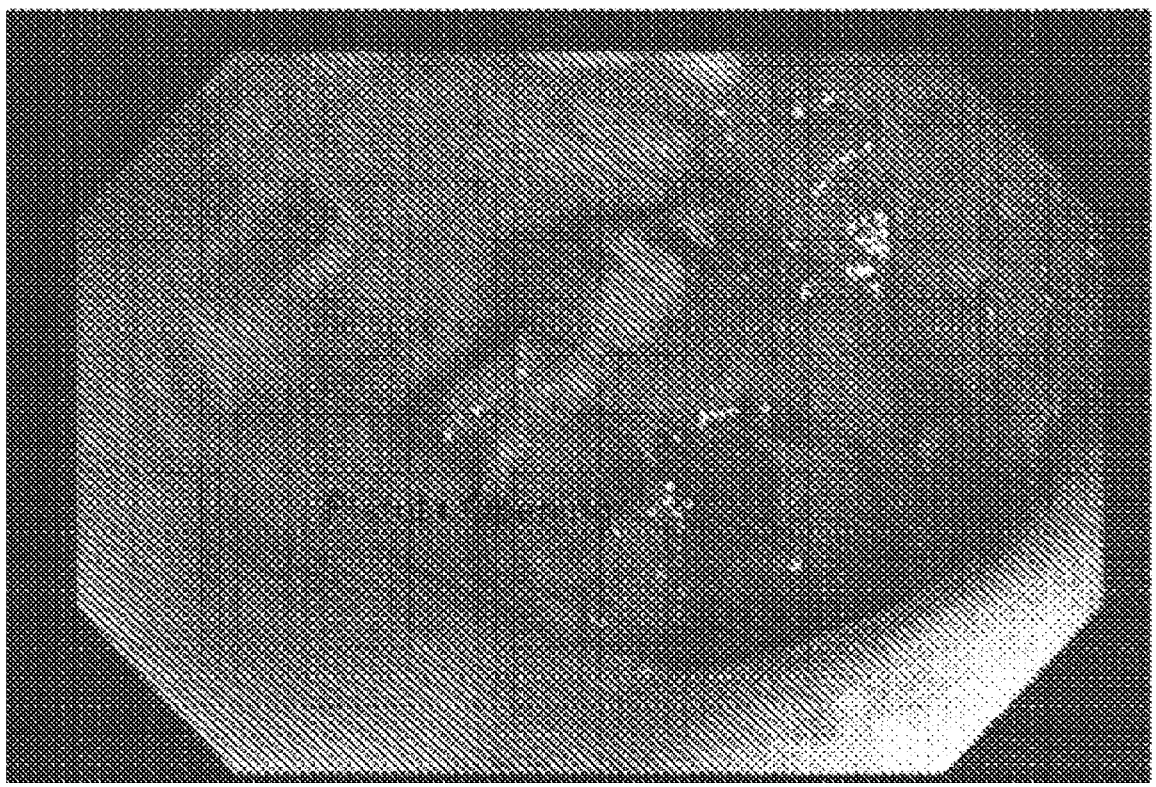
FIG. 3 illustrates an image of a recto vaginal fistula before treatment with an exemplary Pre triple therapy as provided herein.
Figure 4:
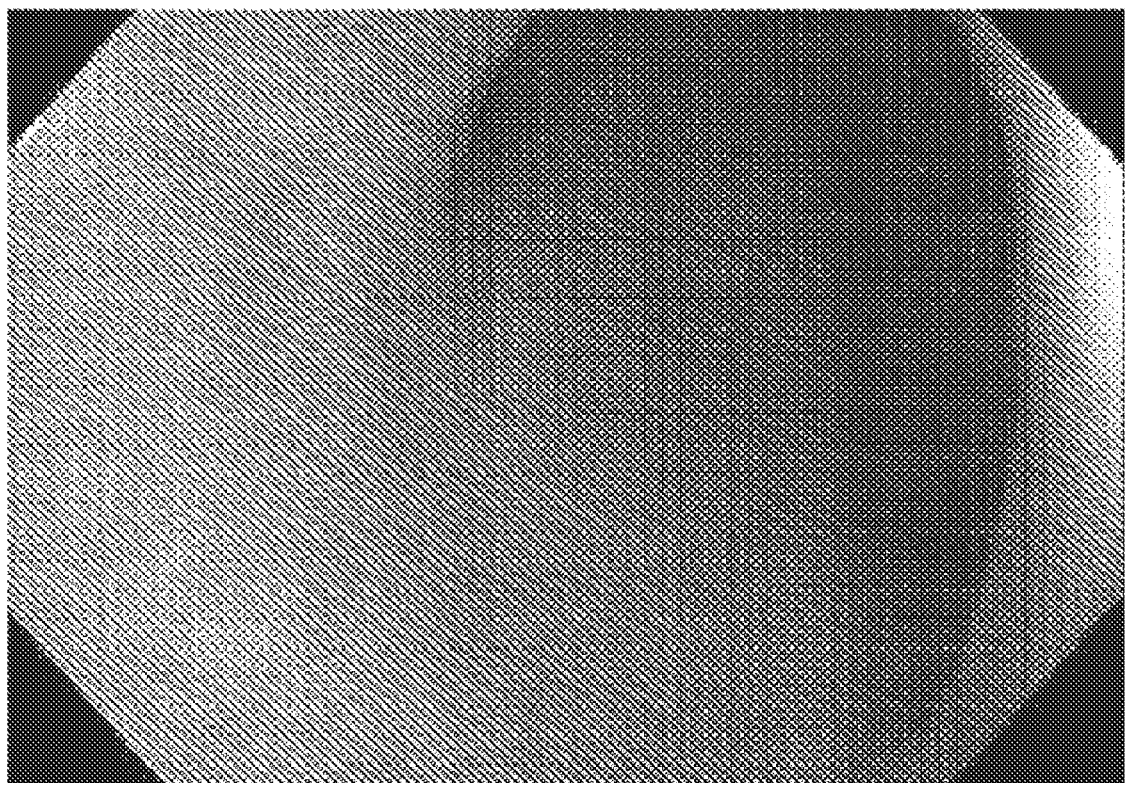
FIG. 4 illustrates an image of a completely healed mucosa after treatment of the recto vaginal fistula with an exemplary Pre triple therapy as provided herein.

In alternative embodiments, the invention provides a "triple combination" therapy for treating, ameliorating and preventing Crohn's Disease and complications of Crohn's Disease, such as a fistulae (or any tract or communication between anatomically distinct sites that do not normally communicate with each other) or related disorders and conditions in mammals, such as paratuberculosis in mammals, or Johne's disease; and compositions for practicing same. In alternative embodiments, the methods and uses of the invention for treating, ameliorating and preventing a Crohn's Disease (CD) and complications of Crohn's Disease, or related disorders and conditions in mammals, such as paratuberculosis in mammals, or Johne's disease, comprises administration to an individual in need thereof:

(1) an anti-TNFα composition, or a composition capable of (down) modulating TNFα activity, including for example, an Anti-TNFα product able to cause autophagy/apoptosis in cells that contain MAP; including e.g., infliximab (e.g., a REMICADE™, Janssen Biotech, Inc.), adalimumab (e.g., a HUMIRA™, Abbvie, North Chicago, Ill.), certolizumab (or certolizumab pegol, e.g., a CIMZIA™), golimumab (e.g., a SIMPONI™), basiliximab (e.g., a SIMULECT™), daclizumab (e.g., a ZENAPAX™), omalizumab (a XOLAIR™), or any combination thereof;

(2) Hyperbaric Oxygen Treatment, or HBOT, the medical use of oxygen at a level higher than atmospheric pressure, for example at a pressure of about 100% oxygen, or between about 90% and 100% oxygen, at 2.5 atm absolute, or between about 2 and 3 atm absolute, for about 90 minutes or between about 1 hour and 2 hours per session or treatment; and (3) an anti *Mycobacterium avium* sub species *paratuberculosis* (MAP) (also called *M. paratuberculosis* or *M. avium* ssp.) (an anti-MAP) agent, composition or therapy, for example: a macrolide antibiotic; or a rifabutin and a macrolide antibiotic; or a rifabutin (e.g., a MYCOBUTIN™), a macrolide antibiotic and a clofazimine; or a combination of a rifabutin, a clarithromycin and a clofazimine (e.g., a LAMPRENE™); where the macrolide antibiotic can be a clarithromycin (e.g., a TRUCLAR™, CRIXAN™ CLARITT™, CLARAC™ BIAXIN™ KLARICID™ KLACID™, KLARAM™, KLABAX™, CLARIPEN™, CLAREM™, CLARIDAR™ FROMILID™, CLACID™ CLACEE™ VIKROL™ INFEX™ CLARIWIN™, RESCLAR™, RANBAXY™ or a CLARIHEXAL™), a dirithromycin (e.g., a DYNABAC™), a roxithromycin (e.g., a XTHROCIN™, ROXL-150™, ROXO™, SURLID™), a telithromycin (e.g., a KETEK™), an azithromycin (e.g., a ZITHROMAX™, a AZITHROCIN™), a troleandomycin (e.g., a TRIOCETIN™, TEKMISIN™) or a mixture or combination thereof. In alternative embodiments, the anti-MAP treatment component comprises administration of a nitroimidazole antibiotic such as metronidazole (e.g., a 5-nitroimidazole, or a FLAGYL™). In alternative embodiments, the anti-MAP treatment component comprises administration of a fluoroquinolone antibiotic such as a ciprofloxacin (e.g., a CILOXAN™, a CIPRO™, a NEOFLOXIN™). In alternative embodiments, the anti-MAP treatment component comprises administration of a nitroimidazole antibiotic (e.g., metronidazole or 5-nitroimidazole) and a fluoroquinolone antibiotic such as a ciprofloxacin. In alternative embodiments, the anti-MAP treatment component comprises administration of a rifaximin (e.g., a XIFAXAN™, a XIFAXANTA™, a NORMIX™) or a rifamycin (e.g., rifamycin B).

In alternative embodiments, the administration of these treatments and medications can be in any order, or simultaneously. For example, in alternative embodiments the anti-TNFα composition, or a composition capable of (down) modulating TNFα activity, can be given before, with or after administration of the anti-MAP drug. In alternative embodiments, anti-TNFα composition and anti-MAP can be administered either: before; after; during; or before and after; or before, during and after, the Hyperbaric Oxygen Treatment, or HBOT. This scheduling or dosage regimen may vary from patient to patient, or mammal to mammal, or even with one patient, depending on the condition of the patient, the patient's response to treatment, etc.

In one embodiment, anti-MAP therapy precedes the anti-TNFα composition (e.g., infliximab) therapy, for example, in patients or mammals who have *Mycobacterium tuberculosis* or *Mycobacterium bovis*, or who are infected by another *Mycobacterium*. If patients that have tuberculosis are treated with anti-TNFα antibodies, they can develop a disseminated disease (called miliary tuberculosis) which is often fatal. However, when combined with a very powerful anti-tuberculosis antibiotic combination, this condition is prevented.

In another embodiment, anti-MAP therapy precedes the anti-TNFα composition (e.g., infliximab) therapy in patients with "latent tuberculosis", including patients who have been immunized or have been passively exposed to small numbers of *Mycobacterium*; these individuals can development a positive QUANTIFERON™ Gold (e.g., QuantiFERON-TB, or QFT) reaction or a positive Mantoux test, and yet do not have active tuberculosis. Usually, for patients with latent tuberculosis, treatment with an anti-TNFα agent such as infliximab or adalimumab are contra-indicated. This invention allows this subgroup of patients to be safely treated when anti-MAP therapy is administered simultaneously with the anti-TNFα therapy of this invention, or if the anti-MAP therapy is taken weeks to months beforehand.

In another embodiment, the "triple combination" therapy of this invention, including e.g., hyperbaric oxygen, anti-TNFα medication and anti-MAP medication, is particularly useful in healing a Crohn's related fistulae, whether it be bowel to bowel, bowel to bladder, rectum to vagina, or rectum to the skin. While the invention is not limited by any particular mechanism of action, the Hyperbaric Oxygen and the antibiotics are able to arrest the growth and stop the growth of deep tissue bacteria, which are usually anaerobic. The "triple combination" therapy of this invention also can inhibit active inflammation and oxidative stress markers, whilst enhancing host (e.g., mammal, patient) antibacterial responses. The "triple combination" therapy of this invention also can stimulate angiogenesis. Infliximab and equivalent acting antibodies themselves have some anti-MAP activity, and in one embodiment an anti-TNFα composition or drug is used as the "anti-MAP" component of the "triple therapy"; and the "triple combination" therapy of this invention can rapidly heal the fistulising Crohn's Disease.

In alternative embodiments, pharmaceuticals, formulations and compositions used to practice the methods of the invention, which comprise anti-TNFα and anti-MAP compositions or drugs, or equivalents thereof, are formulated in delivery forms especially applicable to children, and/or for long-term use, e.g., for adults or for children. In alternative embodiments, compositions of the invention, and compositions used to practice the methods of the invention can take the form of a capsule, a geltab, a pill, a dissolvable wafer, a tablet, a chewable sweet, a lolly (lollypop), a lozenge or a candy, or as a smoothy or a jelly, or ices, ice creams, gelatos, yogurts or drinks.

In alternative embodiments, a delivery form, e.g., a yogurt or a drink, is designed such that the solid component of the anti-TNFα and anti-MAP composition or drug, polymorphic form or analog thereof, or equivalent thereof, is kept without degradation inside a separate sealed space which can be emptied into the delivery vehicle, e.g., drink or yogurt, in a twist top which will release granules of the active agent (e.g., comprising the anti-TNFα and anti-MAP composition or drug, polymorphic form or analog thereof, or equivalent thereof, or mixtures thereof) into the drink, or yogurt or the like, and then dissolves and is eaten or drunk by the child.

In alternative embodiments, the pharmaceuticals, formulations and compositions used to practice the methods of the invention are enterically coated, e.g., in an MMX enteric extend release format, such that active agent (e.g., comprising the anti-TNFα and anti-MAP composition or drug, polymorphic form or analog thereof, or equivalent thereof, or mixtures thereof) is delivered throughout the small through to the large bowel to affect its activity on the desired microbe, e.g., the pathogen that causes Crohn's disease (CD) or related conditions.

In alternative embodiments, a product, a delivery form or formulation of the invention is a flavoured chewable tablet, sweet or candy which the child is directed to take, e.g., more than once a day, e.g., twice or three times daily, to maintain suppression of the CD producing agents in the flora.

Compositions and methods of the invention comprise use of anti-TNFα and anti-MAP compositions or drugs, molecular versions or polymorphic forms, analogs and equivalents thereof. In alternative embodiments, other non-absorbable antibiotics or medications are used in addition to the anti-TNFα and anti-MAP compositions or drugs or equivalents, e.g., other antimicrobials or other ingredients.

Antibiotics, Antimicrobials

In alternative embodiments, a non-absorbable medication is used in addition to an anti-TNFα and anti-MAP composition or drug; for example, a vancomycin, a streptomycin, a fidaxomicin, a gentamicin, a kanamycin, an amikacin, an arbekacin, a neomycin, a netilmicin, a paromomycin, rhodostreptomycin, a tobramycin, an apramycin and mixtures thereof. In alternative embodiments, Ampicillin, Sulbactam or Aztreonam macrolides, e.g., Clarithromycin and Azithromycin can also be used. In alternative embodiments, Nitroimidazoles, such as Metronidazole, Tinidazole can also be employed. In alternative embodiments, other anti-clostridial agents such as Ramoplanan can also be use or combined with rifaximin.

In alternative embodiments, doses (unit dosage forms) of anti-TNFα and anti-MAP compositions or drugs, polymorphic forms or analogs thereof, or equivalents thereof, are from between about 10 mg through or to about 10 gms, or between about 100 mg and 500 mgm, or at 10, 20, 30, 40, 50, 75, 100, 200, 300, 400, 500 or 1000 mgm. Dosages can be adjusted depending on the combination of active agents used, particularly when using two or three or more combination drugs. For example, in alternative embodiments, combination used to practice the compositions or methods of the invention further comprises: streptomycin, Gentamicin, Kanamycin and mixtures thereof; Ampicillin, Sulbactam or Aztreonam and various macrolides, e.g., Clarithromycin; Nitroimidazoles such as Metronidazole; Tinidazole; any anti-clostridial agents such as a Ramoplanan; and/or a Fidaxomicin.

In alternative embodiments, compositions and methods of the invention further comprise use of a rifaximin, or analog or equivalent thereof, with added secondary medications to bolster its activity. In alternative embodiments, compositions and methods of the invention comprise use of rifaximin with vancomycin, or the combination of Rifaximin with Astreonam or Rifaximin with Astreonam together with the beta-lactamase inhibitors. In alternative embodiments these inhibitors are Clavulenic acid, Tazobactam, Sulbactam, LK-157 or equivalents.

In alternative embodiments, compositions and methods of the invention comprise or further comprise use of a rifaximin, polymorphic forms or analogs thereof, or equivalents thereof combined in double or triple therapy format; including, for example, an astreonam, a streptomycin, a gentamicin, a kanamycin or a macrolides, or any combination thereof. In alternative embodiments metronidazole is also added to ensure that any neural streaming toxins where the bacteria reside in the submucosa, is also treated.

In alternative embodiments, antibiotics and/or other antimicrobials are included in or administered with a composition of the invention, e.g., added back to a liquid formulation or preparation of the invention, or cell preparation of the invention. In alternative embodiments, the antimicrobial or antibiotic is or comprises one or more of a: glycopeptide antibiotic, wherein optionally the glycopeptide antibiotic is a vancomycin, a teicoplanin (e.g., TARGOCID™), a telavancin (e.g., VIBATIV™), a bleomycin (e.g., BLENOXANE™), a ramoplanin or a decaplanin; or, a fidaxomycin, a gentamycin, a verdamicin, a mutamicin, a sisomicin, a netilmicin, a retymicin, a neomycin, a streptomycin, a paromomycin, a kanamycin, or an ansamycin, a geldanamycin, an ansamitocin, or an anti-protozoal agent such as nitazoxanide (e.g., DAXON™, DEXIDEX™, KIDONAX™, MITAFAR™, PACOVANTON™, PARAMIX™), a furazolidone (e.g., FUROXONE™, DEPENDAL-M™), a nitroimidazole or metronidazole (e.g., a 5-nitroimidazole, FLAGYL™), a nifuroxazide (e.g., AMBATROL™, ANTINAL™, BACIFURANE™, DIAFURYL™) or a bismuth (e.g., bismuth subsalicylate), also including various groups of antibiotics such as a penicillin (e.g., penicillin G, procaine penicillin, benzathine penicillin or penicillin V), a macrolide (e.g., erythromycin, a clarithromycin (a TRUCLAR™, CRIXAN™, CLARITT™, CLARAC™, BIAXIN™ KLARICID™, KLACID™, KLARAM™, KLABAX™, CLARIPEN™, CLAREM™, CLARIDAR™ FROMILID™, CLACID™, CLACEE™, VIKROL™, INFEX™, CLARIWIN™, RESCLAR™, RANBAXY™ or a CLARIHEXAL™), a dirithromycin (e.g., DYNABAC™), a roxithromycin (e.g., XTHROCIN™, ROXL-150™, ROXO™, SURLID™), a telithromycin (e.g., KETEK™) or an azithromycin such a ZITHROMAX™, AZITHROCIN™), a tetracycline, a cephalosporin, a carbapenem (e.g., imipenem, a meropenem such as MONAN™, MERONEM™), a monobactam, a lincosamide or a clindamycin (e.g., DALACIN™), a quinolone (e.g., a fluoroquinolone) and/or a sulphonamide, a fradicin (e.g., NEOBIOTIC™), or an equivalent thereof or a combination thereof.

In alternative embodiments, the antimicrobial or antibiotic is or comprises one or more of: an aminoglycoside antibiotic (e.g., a gentamycin, a neomycin, a streptomycin, a paromomycin, a verdamicin, a mutamicin, a sisomicin, a netilmicin, a retymicin and/or a kanamycin), amphenicol, ansamycin, beta-lactam (β-lactam), carbapenem, cephalosporin, cephamycin, monobactam, oxacephem, a lincosamide antibiotic (e.g., clindamycin, lincomycin), a macrolide antibiotic (e.g., an azithromycin, clarithromycin, dirithromycin, erythromycin), glycopeptide antibiotic (e.g., a vancomycin, teicoplanin, telavancin, bleomycin, ramoplanin and/or a decaplanin), a polypeptide antibiotic (e.g., actinomycin, such as actinomycin D; bacitracin; bacitracin), tetracycline, or a 2,4-diaminopyrimidine class antibiotic, a clavacin (also known as clairformin, claviform, expansine, clavatin, expansin, gigantin, leucopin, patuline or patulin), or an equivalent thereof or a combination thereof.

Probiotics and Prebiotics

In alternative embodiments, additives that are also included in a composition of the invention (e.g., a liquid preparation embodiment), or a composition used to practice the invention, includes one or more prebiotics such as inulin, lactulose, extracts of artichoke, chicory root, oats, barley, various legumes, garlic, kale, beans or flax and at times prebiotics may include herbs.

In alternative embodiments, additives may include flora components such as *Bacteroidetes, Firmicutes, Bacillus* (e.g., *Bacillus thurigiensis*) or any combination thereof. In alternative embodiments, cultured components are back to the flora to fortify or expand specific genus or species, e.g., *Bacteroidetes, Firmicutes, Bacillus* or *Bacillus thurigiensis*. Probiotics may at times be included as single cultured components. They would avoid multiply cultured components as they lose their implantation characteristics.

Preservatives, Cryoprotectants, Lyoprotectants

In alternative embodiments, to any composition used to practice the invention (e.g., the liquid preparation embodiment, candies, lollies, drinks and the like) may be added various preservatives, cryoprotectants and/or lyoprotectants, including e.g., various polysaccharides or sugars (such as sucrose, fructose, lactose, mannitol), glycerol, polyethylene glycol (PEG), trehalose, glycine, glucose, dextran and/or erythritol. In alternative embodiments, other cryoprotectants that can be used are ethylene glycol, 1,2-Propanediol, Methylcelliosolve, Dimethyl Formamide, or Dimethylsulphoxide Methanol. In alternative embodiments the content of these cryoprotectants are between about 1% and about 50% but generally between about 5% and about 15% is adequate.

Because of the ability to freeze and/or freeze-dry, or spray dry, any composition of the invention, in alternative embodiments there are different types of final products that can be manufactured. In alternative embodiments a product or formulation of the invention is a liquid. In alternative embodiments a product or formulation of the invention is frozen and kept at e.g. minus 80 degrees for usage later given a cryoprotectant is added.

Biofilm Disrupting Compounds

In alternative embodiments, biofilm disrupting compounds added into a composition or formulation (e.g., a liquid preparation embodiment) used to practice a method of the invention. In alternative embodiments, in practicing the methods of the invention, biofilm disrupting compounds are administered before or during (co-administered), or co-formulated with (e.g., in a multilaminated tablet or capsule), or separately formulated, as the administered composition or formulation of the invention. In alternative embodiments, disrupting biofilms are used to separate from the colonic mucosa an adherent polysaccharide/DNA—containing layer, the so-called "biofilm.

In alternative embodiments, other biofilm disrupting components or agents also can be used, e.g., enzymes such as a deoxyribonuclease (DNase), a N-acetylcysteine, an auranofin, alginate lyase, glycoside hydrolase dispersin B; Quorum-sensing inhibitors e.g., ribonucleic acid III inhibiting peptide, *Salvadora persica* extracts, Competence-stimulating peptide, Patulin and penicillic acid; peptides—cathelicidin-derived peptides, small lytic peptide, PTP-7 (a small lytic peptide, see e.g., Kharidia (2011) J. Microbiol. 49(4): 663-8, Epub 2011 Sep. 2), Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea furanones*, N-sulfonyl homoserine lactones and/or macrolide antibiotics or any combination thereof.

In alternative embodiments, biofilm disrupting components or agents are administered before and during the administration of a composition of this invention, e.g., as an FMT, in whatever format or formulation this may take place, for example, as a capsule.

In alternative embodiments, biofilm disrupting agents are added either before treatment and/or during and/or after treatment with a composition of the invention. In alternative embodiments, biofilm disrupting agents are used singly or in combination.

In alternative embodiments, biofilm disrupting agents include particular enzymes and degrading substances including in N-acetylcysteine, deoxyribonuclease (DNase). Others would include Alginate, lyase and Glycoside hydrolase dispersin, Ribonucleic-acid-III inhibiting peptide (RIP), *Salvadora persica* extracts, Competence-stimulating peptide (CSP) Patulin (PAT) and penicillic acid (PA)/EDTA, Cathelicidin-derived peptides, Small lytic peptide, PTP-7, Nitric oxide, Chlorhexidine, Povidone-iodine (PI), Nanoemulsions, Lytic bacteriophages, Lactoferrin/xylitol hydrogel, Synthetic iron chelators, Cranberry components, Curcumin, Acetyl-11-keto-boswellic acid (AKBA), Barley coffee (BC) components, silver nanoparticles, azithromycin, clarithromycin, gentamicin, streptomycin and also Disodium EDTA. Ozone insufflations of the colon can also be used to disrupt the biofilm.

Unit Dosage Forms and Formulations, Foods, and Delivery Vehicles

In alternative embodiments, a composition used to practice the invention (e.g., a liquid preparation embodiment) can be further processed by, e.g., spray-drying or equivalent, e.g., spray-drying in an inert gas or freeze-drying under similar conditions, thus ending up with a powdered product. In alternative embodiments, a composition is manufactured, labelled or formulated as a liquid, a suspension, a spray, a gel, a geltab, a semisolid, a tablet, or sachet, a capsule, a lozenge, a chewable or suckable unit dosage form, or any pharmaceutically acceptable formulation or preparation. In alternative embodiments, a composition of the invention is incorporated into a food or a drink (e.g., a yogurt, ice cream, smoothie), a candy, sweet or lolly, or a feed, a nutritional or a food or feed supplement (e.g., liquid, semisolid or solid), and the like.

For example, a composition used to practice the invention can be manufactured, labelled or formulated as an orally disintegrating tablet as described e.g., in U.S. Pat. App. Publication No. 20100297031. A composition used to practice the invention can be a polyol/thickened oil suspension as described in U.S. Pat. Nos. 6,979,674; 6,245,740. A composition used to practice the invention can be encapsulated, e.g., encapsulated in a glassy matrix as described e.g., in U.S. Pat. App. Publication No. 20100289164; and U.S. Pat. No. 7,799,341. A composition used to practice the invention can be manufactured, labelled or formulated as an excipient particle, e.g., comprising a cellulosic material such as microcrystalline cellulose in intimate association with silicon dioxide, a disintegrant and a polyol, sugar or a polyol/sugar blend as described e.g., in U.S. Pat. App. Publication No. 20100285164. A composition used to practice the invention can be manufactured, labelled or formulated as an orally disintegrating tablet as described e.g., in U.S. Pat. App. Publication No. 20100278930. A composition used to practice the invention can be manufactured, labelled or formulated as a spherical particle, as described e.g., in U.S. Pat. App. Publication No. 20100247665, e.g., comprising a crystalline cellulose and/or powdered cellulose. A composition used to practice the invention can be manufactured, labelled or formulated as a rapidly disintegrating solid preparation useful e.g. as an orally-disintegrating solid preparation, as described e.g., in U.S. Pat. App. Publication No. 20100233278. A composition used to practice the invention can be manufactured, labelled or formulated as a solid preparation for oral application comprising a gum tragacanth and a polyphosphoric acid or salt thereof, as described e.g., in U.S. Pat. App. Publication No. 20100226866.

A composition used to practice the invention can be manufactured, labelled or formulated using a water soluble polyhydroxy compound, hydroxy carboxylic acid and/or polyhydroxy carboxylic acid, as described e.g., in U.S. Pat. App. Publication No. 20100222311. A composition used to practice the invention can be manufactured, labelled or formulated as a lozenge, or a chewable and suckable tablet or other unit dosage form, as described e.g., in U.S. Pat. App. Publication No. 20100184785.

A composition used to practice the invention can be manufactured, labelled or formulated in the form of an agglomerate, as described e.g., in U.S. Pat. App. Publication No. 20100178349. A composition used to practice the invention can be manufactured, labelled or formulated in the form of a gel or paste, as described e.g., in U.S. Pat. App. Publication No. 20060275223. A composition used to practice the invention can be manufactured, labelled or formulated in the form of a soft capsule, as described e.g., in U.S. Pat. No. 7,846,475, or U.S. Pat. No. 7,763,276.

Polyols used in compositions used to practice the invention can be micronized polyols, e.g., micronized polyols, e.g., as described e.g., in U.S. Pat. App. Publication No. 20100255307, e.g., having a particle size distribution ($d_{50}$) of from 20 to 60 μm, and a flowability below or equal to 5 s/100 g, or below 5 s/100 g.

Gradual or Delayed Release Formulations

In alternative embodiments, compositions used to practice the invention are formulated for delayed or gradual enteric release comprising at least one active agent (e.g., a formulation or pharmaceutical preparation of the invention) formulated with a delayed release composition or formulation, coating or encapsulation. In alternative embodiments, formulations or pharmaceutical preparations of the invention are designed or formulated for delivery of active ingredient (e.g., an anti-TNFα composition or drug or anti-MAP agent in its various molecular versions or polymorphic forms, including for example, the extended intestinal release forms for delivery to the distal small bowel and/or the colon. Thus, for this embodiment, it is important to allow the active ingredient to pass the areas of danger, e.g., stomach acid and pancreatic enzymes and bile, and reach undamaged to be viable in the distal small bowel and especially the colon. In alternative embodiments, a formulation or pharmaceutical preparation used to practice the invention is a liquid formulation, a microbiota-comprising formulation of the invention and/or a frozen or a freeze-dried version thereof. In alternative embodiments, preferably for the encapsulated format, all are in powdered form.

In alternative embodiments, compositions of the invention are formulated for delayed or gradual enteric release using cellulose acetate (CA) and polyethylene glycol (PEG), e.g., as described by Defang et al. (2005) Drug Develop. & Indust. Pharm. 31:677-685, who used CA and PEG with sodium carbonate in a wet granulation production process.

In alternative embodiments, compositions used to practice the invention are formulated for delayed or gradual enteric release using a hydroxypropylmethylcellulose (HPMC), a microcrystalline cellulose (MCC) and magnesium stearate, as described e.g., in Huang et al. (2004) European J. of Pharm. & Biopharm. 58: 607-614).

In alternative embodiments, compositions used to practice the invention are formulated for delayed or gradual enteric release using e.g., a poly(meth)acrylate, e.g. a methacrylic acid copolymer B, a methyl methacrylate and/or a methacrylic acid ester, a polyvinylpyrrolidone (PVP) or a PVP-K90 and a EUDRAGIT® RL PO™, as described e.g., in Kuksal et al. (2006) AAPS Pharm. 7(1), article 1, E1 to E9.

In alternative embodiments, compositions used to practice the invention are formulated for delayed or gradual enteric release as described in U.S. Pat. App. Pub. 20100239667. In alternative embodiments, the composition comprises a solid inner layer sandwiched between two outer layers. The solid inner layer can comprise a formulation or pharmaceutical preparation of the invention and one or more disintegrants and/or exploding agents, one or more effervescent agents or a mixture. Each outer layer can comprise a substantially water soluble and/or crystalline polymer or a mixture of substantially water soluble and/or crystalline polymers, e.g., a polyglycol. These can be adjusted in an exemplary composition of the invention to achieve delivery of the living components of an FMT distally down the bowel.

In alternative embodiments, compositions used to practice the invention are formulated for delayed or gradual enteric release as described in U.S. Pat. App. Pub. 20120183612, which describes stable pharmaceutical formulations comprising active agents in a non-swellable diffusion matrix. In alternative embodiments, a formulation or pharmaceutical preparation used to practice the invention is released from a matrix in a sustained, invariant and, if several active agents are present, independent manner and the matrix is determined with respect to its substantial release characteristics by ethylcellulose and at least one fatty alcohol to deliver bacteria distally.

In alternative embodiments, a formulation or pharmaceutical preparation used to practice the invention is formulated for delayed or gradual enteric release as described in U.S. Pat. No. 6,284,274, which describes a bilayer tablet containing an active agent (e.g., an opiate analgesic), a polyalkylene oxide, a polyvinylpyrrolidone and a lubricant in the first layer and a second osmotic push layer containing polyethylene oxide or carboxy-methylcellulose.

In alternative embodiments, a formulation or pharmaceutical preparation used to practice the invention is formulated for delayed or gradual enteric release as described in U.S. Pat. App. Pub. No. 20030092724, which describes sustained release dosage forms in which a nonopioid analgesic and opioid analgesic are combined in a sustained release layer and in an immediate release layer, sustained release formulations comprising microcrystalline cellulose, EUDRAGIT RSPO™, CAB-O-SIL™, sodium lauryl sulfate, povidone and magnesium stearate.

In alternative embodiments, a formulation or pharmaceutical preparation used to practice the invention is formulated for delayed or gradual enteric release as described in U.S. Pat. App. Pub. 20080299197, describing a multi-layered tablet for a triple combination release of active agents to an environment of use, e.g., in the GI tract. In alternative embodiments, a multi-layered tablet is used, and it can comprise two external drug-containing layers in stacked arrangement with respect to and on opposite sides of an oral dosage form that provides a triple combination release of at least one active agent. In one embodiment the dosage form is an osmotic device, or a gastro-resistant coated core, or a matrix tablet, or a hard capsule. In these alternative embodiments, the external layers may contain biofilm dissolving agents and internal layers the living bacteria.

In alternative embodiments, a formulation or pharmaceutical preparation used to practice the invention is formulated as multiple layer tablet forms, e.g., where a first layer provides an immediate release of a formulation or pharmaceutical preparation of the invention and a second layer provides a controlled-release of another (or the same) formulation or pharmaceutical preparation of the invention, or another active agent, as described e.g., in U.S. Pat. No. 6,514,531 (disclosing a coated trilayer immediate/prolonged release tablet), U.S. Pat. No. 6,087,386 (disclosing a trilayer tablet), U.S. Pat. No. 5,213,807 (disclosing an oral trilayer tablet with a core comprising an active agent and an intermediate coating comprising a substantially impervious/impermeable material to the passage of the first active agent), and U.S. Pat. No. 6,926,907 (disclosing a trilayer tablet that separates a first active agent contained in a film coat from a core comprising a controlled-release second active agent formulated using excipients which control the drug release, the film coat can be an enteric coating configured to delay the release of the active agent until the dosage form reaches an environment where the pH is above four).

In alternative embodiments, a formulation or pharmaceutical preparation used to practice the invention is formulated for delayed or gradual enteric release as described in U.S. Pat. App. Pub. 20120064133, which describes a release-retarding matrix material such as: an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinylacetates, polyvinylacetate copolymers or any combination. In alternative embodiments, spherical pellets are prepared using an extrusion/spheronization technique, of which many are well known in the pharmaceutical art. The pellets can comprise one or more formulations or pharmaceutical preparations of the invention, e.g., the liquid preparation embodiment.

In alternative embodiments, a formulation or pharmaceutical preparation used to practice the invention is formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In alternative embodiments, a formulation or pharmaceutical preparation used to practice the invention is a powder that can be included into a tablet or a suppository. In alternative embodiments, a formulation or pharmaceutical preparation of the invention can be a 'powder for reconstitution' as a liquid to be drunk placed down a naso-duodenal tube or used as an enema for patients to take home self-administer enemas for colitis for example. In alternative embodiments, a formulation or pharmaceutical preparation used to practice the invention is micro-encapsulated, formed into tablets and/or placed into capsules, especially enteric-coated capsules.

In alternative embodiments, in practicing the methods of the invention, biofilm disrupting compounds are administered before or during (co-administered), or co-formulated with a composition or formulation of the invention. For example, in alternative embodiments, a composition or formulation of the invention and a biofilm disrupting compound (and/or any other alternative component of the invention, as discussed herein) are co-formulated, e.g., as multiple layer tablet form or as a multi-laminated tablet or capsule. In alternative embodiments of methods of the invention, biofilm disrupting compounds are separately formulated.

Feeds, Drinks, Candies, Nutritional or a Food or Feed Supplements

In alternative embodiments, a formulation or pharmaceutical preparation used to practice the invention is incorporated into a food, a feed, a candy (e.g., a lollypop or a lozenge) a drink, a nutritional or a food or feed supplement (e.g., liquid, semisolid or solid), and the like, as described e.g., in U.S. Pat. App. Publication No. 20100178413. In one embodiment, a formulation or pharmaceutical preparation of the invention is incorporated into (manufactured as) a beverage as described e.g., in U.S. Pat. No. 7,815,956. For example, a composition used to practice the invention is incorporated into a yogurt, an ice cream, a milk or milkshake, a "frosty", "snow-cone", or other ice-based mix, and the like.

In alternative embodiments, a formulation or pharmaceutical preparation used to practice the invention is a freeze-dried powder form added to a food, e.g., a yogurt, an ice cream, a milk or milkshake, a "frosty", "snow-cone", or other ice-based mix, and the like. In one form of this invention it can be kept in a lid-storage (e.g., of a yogurt or ice cream) such that when it is twisted the powder falls into the product or formulation (e.g., yoghurt or ice cream) and then it can be stirred so as not to have the powder ferment 'standing on the shelf'. Various flavourings can be added. In alternative embodiments, this is particularly important for administration of a composition of the invention, e.g., a wild type microbiota or a cultured bacteria, to a very young individual and/or a patient with autism or related disease or condition.

In alternative embodiments, these exemplary products are important when administered to children or babies who may have acquired various pathogenic or abnormal bacteria.

Packaging

The invention provides compositions, including preparations, formulations and/or kits, comprising combinations of ingredients, as described herein. In alternative embodiments, these combinations can be mixed and administered together, or alternatively, they can be an individual member of a packaged combination of ingredients, e.g., as manufactured in a separate package, kit or container; or, where all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package is made up of two separate elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In one embodiment, the invention also provides a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside. These can be hard to open by hand, so a pair of scissors or a sharp knife may be required to open.

In one aspect, blister packaging comprises at least two or three or more components (e.g., is a multi-ingredient combination of the invention): a thermoformed "blister" which houses multi-ingredient combination of the invention, and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or as large as you would like, but there are limitations and cost considerations in going to an oversized blister card. Conventional blister packs can also be sealed (e.g., using an AERGO 8 DUO™, SCA Consumer Packaging, Inc., DeKalb Ill.) using regular heat seal tooling. This alternative aspect, using heat seal tooling, can seal common types of thermoformed packaging.

Blister Packaging

In alternative embodiments, combinations of ingredients of compositions of the invention, or combinations of ingredients for practicing methods of the invention, can be packaged alone or in combinations, e.g., as "blister packages" or as a plurality of packettes, including as lidded blister packages, lidded blister or blister card or packets or packettes, or a shrink wrap.

In alternative embodiments, laminated aluminium foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminium (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminium (e.g., alufoil) lidding material. In one aspect, hermetically-sealed high barrier aluminium (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

In alternative embodiments, any of the invention's multi-ingredient combinations or products of manufacture, including kits or blister packs, include memory aids to help remind patients when and how to take the drug. This safeguards the drug's efficacy by protecting each tablet, geltab or pill until it is taken; gives the product or kit portability, makes it easy to take a dose anytime or anywhere.

REFERENCES

Campbell J, Borody T J, Leis S. The many faces of Crohn's Disease: latest concepts in etiology. Open Journal of Internal Medicine 2012 [in press]

Gitlin L, Borody T J, Chamberlin W, Campbell J. *Mycobacterium avium* ss *paratuberculosis*-Associated Diseases: Piecing the Crohn's Puzzle Together. J Clin Gastroenterol 2012 [in press]

Bach H, Rosenfeld G, Bressler B. Treatment of Crohn"s Disease patients with infliximab is detrimental for the survival of *Mycobacterium avium* ssp. *paratuberculosis* within macrophages and shows a remarkable decrease in the immunogenicity of mycobacterial proteins. J Crohn's Colitis 2012 [published online].

Shafran I, Kugler L, El-Zataari F A et al. Open clinical trial of rifabutin and clarithromycin therapy in Crohn"s Disease. Dig Liver Dis 2002; 34(1): 22-8.

Borody T J, Leis S, Warren E F et al. Treatment of severe Crohn's disease using antimycobacterial triple therapy—approaching a cure? Dig Liver Dis 2002; 34(1): 29-38.

The invention will be further described with reference to the following examples; however, it is to be understood that the invention is not limited to such examples.

EXAMPLES

Example 1: Exemplary Treatments of Crohn's Related Fistulae by Administration of the "Triple Combination Therapy" of the Invention A 32 year (yr) old male with a 3 yr history of Crohn's disease (CD), presented with diarrhea, urgency, perianal tenderness with discharge from a high left-sided posterior and a right anterior fistulae that had 'setons' in situ. The entire colon was inflamed, with Crohn's ulcers destroying areas of haustrations. During combination therapy the 'setons' were removed. At 6 weeks, complete healing of both fistulae was achieved demonstrated by MRI with only scarring present. Inflammatory markers normalized and the patient continued Anti-MAP therapy.

A 32 yr old female with a 22 yr history of CD complicated by a recto-vaginal fistula presented with severe dyspareunia and wind passage through to the vagina during bowel evacuation. The patient also reported frequent, urgent loose motions, tenesmus, blood and mucus. On colonoscopy, active, ulcerating CD was confirmed with a visible fistula opening. After 3 months of combined therapy, she reported increased energy, resolution of bowel symptoms and the return of previously absent menstruation. Complete rectal and vaginal fistula healing was observed on colonoscopy. Subsequent MRI showed disappearance of the original focal abnormality in the ano-rectal area, with no gas-containing locus, and absence of the recto-vaginal fistula.

Example 2: Exemplary Treatments of Crohn's Related Fistulae by Administration of the "Triple Combination Therapy" of the Invention In one alternative embodiment, a treatment of the invention for patients with documented CD (+/−fistulae) comprise of a combination of:

Infliximab (5 mg/kg given as an IV induction regimen at 0, 2, and 6 weeks (followed by a maintenance regimen of 5 mg/kg every 8 weeks if needed—typically a the number of doses range from 3 to 9).

Anti-MAP therapy continuously from week 0 (typically maintained from 3 months to 2 or more years).

In alternative embodiments, in an adult this would be clofazimine 100 mg/d; rifabutin 450-600 mg/d; clarithromycin 1 g/day; with additional metronidazole 400-800 mg/d or ethambutol 800 mg/d or Pyrazinamide 500 mg to 2 gm—depending on adverse effects.

In alternative embodiments, in a child this would be clofazamine, rifabutin 5 mg/kg/day orally, clarithromycin 7.5 mg/kg/dose (maximum 500 mg/dose) orally twice daily, metronidazole 7.5 to 30 mg/kg/day orally in 2 to 3 divided doses daily HBOT concurrently, in alternative embodiments, between about 20 to 30 daily sessions at about 2.4 ATM.

Example 3: Exemplary Treatments of Crohn's Related Fistulae by Administration of the "Triple Combination Therapy" of the Invention This example described the effectiveness of exemplary "triple combination" therapies" of the invention, where patients were treated with Infliximab, Hyperbaric Oxygen Therapy (HBOT) and Anti-MAP treatment. A series of 6 patients, where each patient reported had failed conventional treatment, was used. This example describes the effectiveness of an exemplary "triple combination" therapy" of the invention in healing a higher proportion of fistulae for a longer period by using the invention's multi-modal approach.

Methods: Treatment with Infliximab, Hyperbaric Oxygen Therapy (HBOT) and Anti-MAP treatment were used in a series of 6 patients. Each patient reported had failed conventional treatment.

Results: On completion of the combination therapy, all 6 patients achieved complete healing of perianal and recto-vaginal fistulae alongside maintained resolution of their Crohn's disease in general, with one patient treated 8 years ago.

Conclusions: Each of the 3 treatments is known to contribute individually to a small extent towards amelioration of Crohn's disease and the complication of fistulae specifically. However when combined, higher rates of healing of recalcitrant fistulae are achieved with 100% success reported in our case series. To date around 18 patients with previously recalricant, who have now all achieved complete healing and remission of their disease. This process is thought to occur through the targeting of inflammation, blood flow, anaerobic bacteria and MAP respectively.

Material and Methods: In this case series, patients with documented CD and fistulae were treated with a combination of infliximab and continuous Anti-MAP therapy (clofazimine 100 mg/d; rifabutin 450-600 mg/d; clarithromycin 1 g/day; with additional metronidazole 400-800 mg/d or ethambutol 800 mg/d—depending on adverse effects) and HBOT concurrently (20-30 daily sessions at 2.4 ATM).

This study prospectively followed 6 CD patients with severely active CD and intractable fistulae, who were previously non-responsive to standard CD treatments that had included steroids, thiopurines, methotrexate and biologics. Response was assessed by change in clinical symptoms, colonoscopic findings, and pre- and post-treatment magnetic resonance imaging (MRI). With an accuracy of 90%, MRI is considered the preferred imaging modality for detecting and classifying fistulizing perianal disease[10].

Results:
Case Series

TABLE 1

Summary of Patients and Their Treatment and Response

| Patient | Age | Type, Number and duration of Fistulae | Previous Treatment | Number Of Infliximab Doses | Anti-MAP | Number of HBOT | Fistula Resolution Achieved |
|---|---|---|---|---|---|---|---|
| C.I. | 24 | Multiple (>3) rectum-to-rectum fistulae and abscesses | Azathioprine | 3 | Rifabutin Clofazimine Clarithromycin Ethambutol Ciprofloxacin Metronidazole | 30 | Yes with healed mucosa persisting at review 10 months later |
| S.F. | 32 | High left sided posterior and right superficial anterior perianal/rectal fistula | Seton insertion | 3 | Rifabutin Clofazimine Clarithromycin Ethambutol Ciprofloxacin Metronidazole | 21 | Yes with healed mucosa after 6 weeks. No seton |
| A.B. | 32 | Recto-vaginal | Infliximab | 4 | Rifabutin Clofazimine Clarithromycin Pyrazinamide Metronidazole | 21 | Yes with healed mucosa Absence of recto-vaginal wind passage |

TABLE 1-continued

Summary of Patients and Their Treatment and Response

| Patient | Age | Type, Number and duration of Fistulae | Previous Treatment | Number Of Infliximab Doses | Anti-MAP | Number of HBOT | Fistula Resolution Achieved |
|---|---|---|---|---|---|---|---|
| K.B. | 31 | Right inter-sphincteric fistula and a posterior anal fissure | Azathioprine Previous bowel resection | 4 | Rifabutin Clofazimine Clarithromycin Ethambutol Metronidazole | 18 | Yes with healed mucosa. Posterior fissure remained but minimal in size at 6 weeks |
| N.V. | 40 | 3 perianal fistulae | Mesalazine Anti-MAP | 3 | Rifabutin Clarithromycin Clofazaimine Ethambutol Ciprofloxacin Azathioprine | 21 | Yes, with healed mucosa and remaining healed at 8 yrs No setons |
| D.H. | 38 | Deep rectal fistula just below the labia | Mesalazine Azathiaprine Prednisolone Seton in situ | 4 | Rifabutin Clofazimine Clarithromycin Ethambutol Metronidazole | 20 | Yes. Rectal fistula had resolved. No seton Small healed introital tract |

Discussion:

This invention for the first time describes use of the combination of an anti-TNFα composition or drug (e.g., an infliximab), HBOT and anti-MAP therapy in fistulizing CD hasn't previously been described. In our small series of patients with intractable fistulae, this therapy achieved near 100% healing. This is significantly higher than comparable data for any of the three therapies alone and any treatments currently available. Up to 35% of patients with Crohn's disease will develop fistulae: of these, 20% are in the perianal region[11]. Fistulae develop between two surfaces such as loops of bowel, bowel and bladder, bowel and vagina, and bowel and skin. They can be classed as 'simple' (superficial, inter- or trans-sphincteric fistulae below the dentate line, a single opening and no anorectal stricture or abscess), or 'complex' (trans-, supra-, or extra-sphincteric fistulae above the dentate line; a fistula with multiple external openings, associated abscess or stricture; or a rectovaginal fistula)[12].

Fistulotomy is not recommended for complex fistulae and resection of the rectum in perianal fistula with permanent colostomy may be necessary in 10-20% of cases[13]. Rectovaginal fistulae have a poor response to infliximab alone, with 14-30% healing vs 46-78% perianal fistulae. A subgroup of these patients will need proctectomy and a permanent stoma[14]. Biologics have to some small extent improved treatment of fistulae—otherwise most are intractable, requiring 'seton' placement to prevent abscess formation.

Infliximab was first used for penetrating Crohn's disease in 1999[15]. The initial phase II and subsequent phase III trials showed that 56-68% of fistulae initially healed in 296 patients[1-2]. In the ACCENT 2 trial, there was a response in 60% of fistulae after 14 weeks, with 36% maintaining closure at 1 year compared with a remarkable 19% on placebo[2]. While the results are impressive, the majority of patients have continued fistulizing activity despite treatment and only a small subset achieve complete long-term healing[16]. Initial response to infliximab can be dramatic but the median duration of fistula closure is approximately 3 months—normally requiring 3 doses of infliximab[17]. Current infliximab therapy for complex perianal fistulae in CD is therefore disappointing especially in achieving complete closure and maintenance of healing[18]

Anti-MAP treatment is increasingly used as a targeted MAP therapeutic[19], the debated infectious etiological CD agent. Although MAP has fulfilled Koch's postulates as the cause of CD[20-22], there is still considerable doubt over its true involvement in CD, largely due to its difficulty in detection. As such, Anti-MAP therapy is a relatively novel treatment rarely utilized by specialists, reminiscent of similar specialist behavior in *Helicobacter pylori*. In not recognizing the role of MAP in CD, despite accumulating evidence, Sartor reflected, "are we repeating the mistake of *H. pylori*"[23] thereby neglecting a viable treatment option in patients with intractable disease.

Slow uptake of anti-MAP treatment by gastroenterologists is in part attributed to the poorly constructed trial carried out by Selby et al in 2007[24]. This study used incorrect methods and data analyses that resulted in inaccurate conclusions[25-29]. As with Tuberculosis (TB), MAP demands a complex combination antibiotic regime to prevent resistance during treatment, given this is the slowest known reproducing organism[30]. Anti-MAP treatment has been reported to induce fistula healing in CD. Shafran et al (2001) treated 10 MAP-positive patients with fistulae. All fistulae healed by 32 weeks using rifabutin, clarithromycin and 2 probiotics[8]. Similarly, Borody et al (2006) showed fistula healing in 3 out of 5 patients treated with Anti-MAP therapy[9].

Hyperbaric Oxygen Therapy is a novel treatment targeting anaerobic bacteria colonizing CD fistulae. HBOT is predominantly used for accelerating the healing of tissue necrosis[31] e.g. diabetic foot ulcers and sports injuries. Fistulae are thought to persist due to ongoing ischemia and persistent colonization with anaerobic microorganisms[32]. Brady et al reported a patient with an 8-year refractory CD fistula that healed with one session of HBOT[33]. Higher atmospheric oxygen environments create unsuitable conditions for anaerobe survival. HBOT also inhibits active inflammation, in part by suppressing TNF-alpha, IL-1 and IL-6 and enhancing host antibacterial responses[34,35]. Furthermore, HBOT decreases neopterin, myeloperoxidase activity and oxidative stress markers, whilst stimulating angiogenesis[36]. It has the ability to optimize fibroblast/ collagen proliferation and white blood cell activity, otherwise limited during periods of hypoxia[37]. Minimal adverse effects exist with HBOT[38]. Sporadic case reports of Crohn's perianal disease achieving complete healing on HBOT and antibiotics (not anti-MAP)[3] exist. Two studies have reported uncontrolled prospective trials involving a subset of refractory CD patients. In one, 10 patients with refractory perianal Crohn's disease underwent 90 min daily sessions for 20 days at a pressure of 2.5 ATM. After 2 courses, 50% of patients experienced complete healing, with a 3rd course increasing this rate to 70%. At 18 months follow up there was no evidence of recurrence[4]. Similar results were shown in another trial with 10 patients[5]. Iezzi et al reported on 14 patients with abdominal enterocutaneous or perianal fistulae and skin complications, including pyoderma gangrenosum, that were treated with HBOT. Eleven, including those who had been refractory to pharmacological therapy, had a satisfactory response[6].

In conclusion, these studies demonstrate that use of this exemplary "triple combination" therapy of the invention comprising use of the three fistulae therapies Infliximab, HBOT and Anti-MAP (all of which are only partially effective when used alone) resulted in much higher rates of healing.

REFERENCES

1). Present D, Rutgeerts P, Targan S, et al. *"Infliximab for the treatment of fistulas in patients with Crohn's disease"*. The New England Journal of Medicine 1999 May 6; 340(18): 1398-405
2). Sands B, Anderson F, Bernstein C et al. *"Infliximab maintenance therapy for fistulizing Crohn's disease"*. The New England Journal of Medicine 2004 Feb. 26; 350 (9): 876-85.
3). Sipahi A M, Damião A O, et al. *Hyperbaric oxygen: a new alternative in the treatment of perianal Crohn's disease*. Rev Hosp Clin Fac Med Sao Paulo. 1996 September-October; 51(5):189-91.
4). Lavy A, Weisz G, Adir Y et al. *Hyperbaric Oxygen for perianal Crohn's disease*. J Clin Gastroenterol. 1994 October; 19(3):202-5.
5). Colombel J F, Mathieu D, Bouault J M et al. *Hyperbaric oxygenation in severe perianal Crohn's disease*. Dis Colon Rectum. 1995 June; 38 (6):609-14.).
6). Iezzi L E et al. *Crohn's disease and hyperbaric oxygen therapy*. Acta Cir Bras. 2011; 26 Suppl 2:129-32.
7). Cheng W, Tsai W. *Microbiological Analysis of Perianal Abscess and its Treatment*. J Soc Colon Rectal Surgeon (Taiwan) March 2010; 21:37-42
8). Shafran I, Kugler L J, Sandoval J E. *Fistula healing in MAP positive Crohn's disease patients following rifabutin and macrolide antibiotic therapy. Gastroenterology, April 2001.* Volume 120, Issue 5, Supplement 1, Page A279.
9). Borody T et al. *Anti-Mycobacterium SS Paratuberculosis (MAP) Therapy and Fistula Closure in Patients with Severe Crohn's disease*. Abstract AM J Gastro 2006:101: s440.
10). Schwartz D A, Wiersema M J, Dudiak K M et al. *A comparison of endoscopic ultrasound, magnetic resonance imaging, and exam under anesthesia for evaluation of Crohn's perianal fistulas*. Gastroenterology. 2001; 121: 1064-1072.
11). Eglinton T W, Barclay M L, Gearry R B et al. *The spectrum of perianal Crohn's disease in a population-based cohort*. Dis Colon Rectum. 2012 July; 55(7):773-7.
12). Lewis R and Maron D. *Efficacy and Complications of Surgery for Crohn's Disease*. Gastroenterol Hepatol. September 2010; 6(9): 587-596.
13). Sandborn W J, Fazio V W, Feagan B G et al. *American Gastroenterological Association Clinical Practice Committee AGA technical review on perianal Crohn's disease*. Gastroenterology. 2003; 125:1508-2.
14). Russel M G, Stockbrugger R W. Epidemiology of Inflammatory Bowel Disease: an update. Scand J. Gastroenterol. 1996 May, 31:417-427.
15). Present D H. *Review article: the efficacy of infliximab in Crohn's disease—healing of fistulae*. Aliment Pharmacol Ther. 1999 September; 13 Suppl 4:23-8; discussion 38.
16). Bourikas L A, Koutroubakis I E. *Anti-TNF and fistulizing perianal Crohn's disease: use in clinical practice*. Curr Drug Targets. 2010 February; 11(2):187-97.
17). Van Den Brande J M, Peppelenbosch M P, Van Deventer S J. *Treating Crohn's disease by inducing T lymphocyte apoptosis*. Ann. N. Y. Acad. Sci 2002 November 973: 166-80.
18). Bode M, Eder S, Schürmann G. *Perianal fistulas in Crohn's disease—biologicals and surgery: is it worthwhile*? Z Gastroenterol. 2008 December; 46(12): 1376-83. Epub 2008 Dec. 3.
19). Campbell J et al. *The many faces of Crohn's Disease: Latest concepts in etiology*. Open Journal of Internal Medicine. 2012, 2(2); 107
20). Abubakar, Myhill D, Aliyu S et al. *Detection of Mycobacterium avium subspecies paratuberculosis from patients with Crohn's disease using nucleic acid techniques: a systematic review and meta-analysis*. Inflam Bowel Dis 2008; 14(3): 401-10.
21). Chamberlin, W., Borody, T., Naser, S. *MAP-associated Crohn's Disease: MAP, Koch's postulates, causality and Crohn's Disease*. Digestive & Liver Disease 2007 August; 39(8):792-794.
22). Hermon-Taylor J. Protagonist. *Mycobacterium avium subspecies paratuberculosis is a cause of Crohn's disease*. Gut. 2001 December; 49(6):755-6.
23). Sartor R B. *Does Mycobacterium avium subspecies paratuberculosis cause Crohn's disease*? Gut. 2005 July; 54(7):896-8.
24). Selby W et al. *Two-year combination antibiotic therapy with clarithromycin, rifabutin, and clofazimine for Crohn's disease. Gastroenterology*. 2007 June; 132(7): 2313-9. Epub 2007 Mar. 21.
25). Behr M, Kapur V. *The evidence for Mycobacterium paratuberculosis in Crohn's disease*. Curr. Opin. Gastroenterol. 2008 January; 24(1), 17-21.2008
26). Kuenstner J T. *The Australian antibiotic trial in Crohn's disease: alternative conclusions from the same study*. Gastroenterology. 2007 November; 133(5):1742-3; author reply 1745-6.
27). Lipton J E, Barash D P. *Flawed Australian CD study does not end MAP controversy*. Gastroenterology. 2007 November; 133(5):1742; author reply 1745-6.
28). Chamberlin W. *Importance of the Australian Crohn's disease antibiotic study*. Gastroenterology. 2007 November; 133(5):1744-5; author reply 1745-6.
29). Gitlin L, Biesacker J. *Australian Crohn's antibiotic study opens new horizons. Gastroenterology.* 2007 November; 133(5):1743-4; author reply 1745-6.
30). Hermon-Taylor J, Bull T J, Sheridan J M et al. *Causation of Crohn's disease by Mycobacterium avium subspecies paratuberculosis*. Can J Gastroenterol. 2000 June; 14(6):521-39.

31). Kranke P, Bennett M H, Martyn-St James M et al. *Hyperbaric oxygen therapy for chronic wounds.* Cochrane Database Syst Rev. 2012 Apr. 18; 4.

32). Sartor, R B. Microbial factors in the pathogenesis of Crohn's disease, ulcerative colitis, and experimental intestinal inflammation. In: Kirsner J B, Shorter R G, eds. *Inflammatory bowel disease.* Williams & Wilkins: Baltimore, 1995: 96-124.

33). Brady C E, Cooley B J, Davis J C. Gastroenterology 1989 September; 97(3):756-60.

34). Noyer C and Brandt L. *Hyperbaric oxygen therapy for perineal Crohn's disease.* American Journal of Gastroenterology (1999) 94, 318-321.

35). Weisz G et al. *Modification of in Vivo and in Vitro TNF α, IL-1, and IL-6 Secretion by Circulating Monocytes During Hyperbaric Oxygen Treatment in Patients with Perianal Crohn's Disease.* J Clin Imm 1997: 17(2); 154.

36). Lin K C, Niu K C et al. *Attenuating inflammation but stimulating both angiogenesis and neurogenesis using hyperbaric oxygen in rats with traumatic brain injury.* J Trauma Acute Care Surg. 2012 March; 72(3):650-9.

37). Sipahi A M, Damião A O, et al. *Hyperbaric oxygen: a new alternative in the treatment of perianal Crohn's disease.* Rev Hosp Clin Fac Med Sao Paulo. 1996 September-October; 51(5):189-91.

38). Rossignol D A. *Hyperbaric oxygen treatment for inflammatory bowel disease: a systematic review and analysis.* Med Gas Res. 2012 Mar. 15; 2(1):6.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating or ameliorating a Crohn's Disease, a complication of a Crohn's Disease, or a Crohn's Disease-related fistulae, comprising administering to an individual in need thereof a therapeutic combination comprising:
   (1) at least one anti-TNFα composition or drug; or at least one composition or drug capable of down-modulating or down-regulating a TNFα activity; and
   (2) at least two anti-*Mycobacterium avium* sub species *paratuberculosis* (MAP) (an anti-MAP) agents.

2. The method of claim 1, wherein the at least one anti-TNFα composition or drug, or the at least one composition or drug capable of down-modulating or down-regulating a TNFα activity comprises: a protein, a peptide or an antibody capable of specifically binding to a TNFα or a TNFα-receptor or TNFα downstream.

3. The method of claim 1, wherein the at least two anti-MAP agents comprise rifabutin.

4. The method of claim 1, comprising administration to an individual or a patient in need thereof:
   (1) at least one anti-TNFα composition or drug, or at least one composition or a drug capable of down-modulating or down-regulating a TNFα activity; and
   (2) at least three anti-*Mycobacterium avium* sub species *paratuberculosis* (MAP) (an anti-MAP) agents.

5. The method of claim 4, wherein the at least three anti-*Mycobacterium avium* sub species *paratuberculosis* agents comprise:
   (a) rifabutin, clofazimine and clofazimine;
   (b) rifabutin, clofazimine and clarithromycin;
   (c) rifabutin, clofazimine and metronidazole or 5-nitroimidazole;
   (d) rifabutin, clofazimine and tinidazole; or
   (e) rifabutin, clofazimine and ciprofloxacin.

6. The method of claim 1, wherein the therapeutic combination is manufactured or formulated as:
   (a) a chewable delivery vehicle, a gum, a gummy, a candy, a lozenge, an ice cream or an ice, or a yogurt, or a unit dosage of an anti-MAP or an anti-TNFα composition, drug, formulation, pharmaceutical or pharmaceutical preparation is formulated as a pediatric unit dosage; or
   (b) a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

7. The method of claim 1, wherein the therapeutic combination comprises or has added to it:
   a flavoring or a sweetening agent, aspartamine, stevia, monk fruit, sucralose, saccharin, cyclamate, xylitol, vanilla, artificial vanilla or chocolate or strawberry flavor, artificial chocolate essence, or a mixture or combination thereof;
   a preservative, a benzoic acid, a potassium sorbate;
   at least one probiotic or prebiotic;
   at least one congealing agent, wherein optionally the congealing agent comprises an arrowroot or a plant starch, a powdered flour, a powdered potato or potato starch, an absorbent polymer, and/or a corn flour or a corn starch;
   at least one an anti-inflammatory agent, wherein optionally the inflammatory agent comprises or is a 4 or a 5-amino-salicylate, an olsalazine, a mesalazine, a sulfasalazine, and/or a balsalazide, or an equivalent thereof or a combination thereof;
   an additive selected from one or more of a saline, a media, a defoaming agent, a surfactant agent, a lubricant, an acid neutralizer, a marker, a cell marker, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient; or
   at least one Biofilm Disrupting Compound.

8. The method of claim 1, wherein the therapeutic combination is formulated as a delayed or gradual enteric release composition or formulation.

9. The method of claim 1, wherein: a unit dosage of the at least one anti-MAP agent or the at least one anti-TNFα composition, drug, formulation, pharmaceutical or pharmaceutical preparation is formulated as unit dosage of between about 10 mg and 1100 mg, or is about 10, 20, 30, 40, 50, 60, 70, 75, 80, 90, 100, 125, 150, 175, 200, 225, 250, 275, 300, 325, 350, 375, 400, 425, 450, 475, 500, 600, 700, 750, 800, 900, 1000 or 1100 or more mg per unit dose, or a unit dosage of the at least one anti-MAP agent.

10. The method of claim 1, wherein a unit dosage of the at least one anti-MAP or the at least one anti-TNFα composition, drug, formulation, is for: a bid (twice a day), tid (three times a day), four times a day, five times a day or six times a day or more, administration.

11. The method of claim 1, wherein the therapeutic composition is formulated as or contained in a product of manufacture.

12. The method of claim 11, wherein the product of manufacture is a delivery vehicle, a container, a syringe, a device or a bag.

13. The method of claim 1, wherein the TNFα activity comprises causing an autophagy or an apoptosis in a cell.

14. The method of claim 1, wherein the therapeutic combination is manufactured or formulated as a pharmaceutical or pharmaceutical preparation.

15. The method of claim 2, wherein the antibody is or comprises: an infliximab; an adalimumab; a certolizumab, certolizumab pegol; a golimumab; a basiliximab; a daclizumab; an omalizumab; or, any combination thereof.

16. The method of claim 8, wherein the formulation comprises a gastro-resistant coating designed to dissolve at a pH of 7 in the terminal ileum.

17. The method of claim 8, wherein the formulation or the therapeutic combination is coated with an acrylic based resin or equivalent, or a poly(meth)acrylate, or a methacrylic acid copolymer B, NF, which dissolves at pH 7 or greater.

18. The method of claim 17, wherein the formulation comprises a multimatrix (MMX) formulation.

19. The method of claim 10, wherein the unit dosage or daily dosage is adjusted to be: about 1000 mg/70 kg a day, or about 14 mg/kg a day, for an adult median dose per day or five times a day for adult use, or for a 70 kg individual would be 200 mg per unit dose; or for a pediatric dosage about 350 mg/25 kg a day, or about 15 to 16 mg/kg, a day; or equivalent, or, five times a day for pediatric use, or for a 25 kg individual about 70 mg per unit dose.

20. The method of claim 1, wherein the at least one anti-TNFα composition or drug is formulated for administration at a daily or once a day dosage of about 100, 125, 150, 175, 200, 225, 250, 275, 300, 325, 350, 375, 400, 425, 450, 475, 500, 600, 700, 750, 800, 900, 1000 or 1100 or more mg per day, or between about 100 and 1100 mg per day.

21. The method of claim 7, wherein the prebiotic comprises an inulin, lactulose, extracts of artichoke, chicory root, oats, barley, various legumes, garlic, kale, beans or flax or an herb.

22. The method of claim 7, wherein the probiotic comprises a cultured or stool-extracted microorganism or bacteria, or a bacterial component.

23. The method of claim 21, wherein the bacteria or bacterial component comprises or is derived from a *Bacteroidetes*, a *Firmicutes*, a *Lactobacilli*, a *Bifidobacteria*, an *E. coli*, or a *Strep fecalis*.

24. The method of claim 7, wherein the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides-cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea furanones*, N-sulfonyl homoserine lactones or any combination thereof.

* * * * *